(12) United States Patent
Kodukula et al.

(10) Patent No.: US 10,179,895 B2
(45) Date of Patent: Jan. 15, 2019

(54) DEVICE FOR FUEL AND CHEMICAL PRODUCTION FROM BIOMASS-SEQUESTERED CARBON DIOXIDE AND METHOD THEREFOR

(71) Applicants: Prasad S Kodukula, Chicago, IL (US); Charles R Stack, Aurora, IL (US)

(72) Inventors: Prasad S Kodukula, Chicago, IL (US); Charles R Stack, Aurora, IL (US)

(*) Notice: Subject to any disclaimer, the term of this patent is extended or adjusted under 35 U.S.C. 154(b) by 211 days.

(21) Appl. No.: 14/886,907

(22) Filed: Oct. 19, 2015

(65) Prior Publication Data

US 2016/0075982 A1 Mar. 17, 2016

Related U.S. Application Data

(62) Division of application No. 12/661,002, filed on Mar. 9, 2010, now Pat. No. 9,593,300.

(Continued)

(51) Int. Cl.

| | |
|---|---|
| *C12M 1/107* | (2006.01) |
| *C12M 3/00* | (2006.01) |
| *C12M 1/00* | (2006.01) |
| *C12M 1/08* | (2006.01) |
| *C12P 5/02* | (2006.01) |
| *C12P 39/00* | (2006.01) |
| *C12M 1/34* | (2006.01) |

(Continued)

(52) U.S. Cl.
CPC ............ *C12M 21/04* (2013.01); *C12M 21/02* (2013.01); *C12M 23/36* (2013.01); *C12M 23/58* (2013.01); *C12M 27/02* (2013.01); *C12M 27/24* (2013.01); *C12M 29/14* (2013.01); *C12M 31/10* (2013.01); *C12M 41/34* (2013.01); *C12M 41/40* (2013.01); *C12P 5/023* (2013.01); *C12P 7/6463* (2013.01); *C12P 19/00* (2013.01); *C12P 21/00* (2013.01); *C12P 39/00* (2013.01); *Y02E 50/343* (2013.01)

(58) Field of Classification Search
CPC ...... C12M 21/02; C12M 27/24; C12M 31/10; C12M 41/40; C12M 41/34; C12P 39/00; C12P 5/023; Y02E 50/343
USPC ................................. 47/1.4; 435/167, 292.1
See application file for complete search history.

(56) References Cited

U.S. PATENT DOCUMENTS

| | | |
|---|---|---|
| 3,303,608 A | 2/1967 | Hannan |
| 4,044,500 A | 8/1977 | Hitzman |

(Continued)

OTHER PUBLICATIONS

High quality biodiesel production from a microalga Chlorella protothecoides by heterotrophic growth in fermenters, by Han Xu, et al., Journal of Biotechnology, May 4, 2006.

(Continued)

*Primary Examiner* — Michael L Hobbs
(74) *Attorney, Agent, or Firm* — Neal, Gerber & Eisenberg LLP

(57) ABSTRACT

A process and apparatus for converting sequestered carbon to fuel, such as methane, and/or materials, such as fermentation substrates, biopolymers, bioplastics, oils, pigments, fibers, proteins, vitamins, fertilizers and animal feed. The apparatus comprises a deep well carbon-sequestering bioreactor coaxially located within a deep well anaerobic bioreactor. Carbon is sequestered into a photosynthetic biomass or a heterotrophic biomass, which is subsequently digested by an anaerobic biomass containing methanogenic microbes, whereby methane is a digestion product.

24 Claims, 4 Drawing Sheets

Related U.S. Application Data

(60) Provisional application No. 61/209,929, filed on Mar. 12, 2009.

(51) Int. Cl.
    C12M 1/06    (2006.01)
    C12P 7/64    (2006.01)
    C12P 19/00   (2006.01)
    C12P 21/00   (2006.01)

(56) References Cited

U.S. PATENT DOCUMENTS

| | | | |
|---|---|---|---|
| 4,217,211 A | 8/1980 | Crane | |
| 4,482,458 A | 11/1984 | Rovel et al. | |
| 5,342,524 A | 8/1994 | Gaddy | |
| 5,413,713 A * | 5/1995 | Day | C02F 3/2806 |
| | | | 210/617 |
| 5,614,378 A | 3/1997 | Yang et al. | |
| 5,618,431 A | 7/1997 | Kondo et al. | |
| 5,650,070 A | 7/1997 | Pollock | |
| 6,024,876 A | 2/2000 | Pannier et al. | |
| 6,416,993 B1 | 7/2002 | Wexler et al. | |
| 6,468,429 B1 | 10/2002 | Pollock | |
| 6,984,323 B2 | 1/2006 | Khudenko | |
| 7,618,813 B2 | 11/2009 | Lee et al. | |
| 7,824,904 B1 * | 11/2010 | Dimanshteyn | C12M 21/02 |
| | | | 362/101 |
| 8,092,680 B2 | 1/2012 | Johnson | |
| 8,097,168 B2 | 1/2012 | Theodore et al. | |
| 8,153,850 B2 | 4/2012 | Hall et al. | |
| 8,372,274 B2 | 2/2013 | Early | |
| 2007/0289206 A1 | 12/2007 | Kertz | |
| 2008/0050800 A1 | 2/2008 | McKeeman et al. | |
| 2008/0096267 A1 | 4/2008 | Howard et al. | |
| 2009/0227003 A1 | 9/2009 | Blotsky et al. | |
| 2009/0321349 A1 | 12/2009 | Offerman et al. | |
| 2011/0183368 A1 * | 7/2011 | Chapman | A01G 7/045 |
| | | | 435/29 |
| 2011/0203992 A1 * | 8/2011 | Liu | C02F 1/286 |
| | | | 210/607 |

OTHER PUBLICATIONS

Analysis of energy conversion characteristics in liquefaction of algae, by Y.F. Yang, Resources Conservation & Recycling, Mar. 19, 2004.
Adaptive Changes in Membrane Lipids of Barophilic Bacteria in Response to Changes in Growth Pressure, by Yutaka Yano, et al., Applied and Environmental Microbiology, Feb. 1998.
Enzymatic Approach to Biodiesel Production, Journal of Agricultural and Food Chemistry, by Casimir C. Akoh, et al., Sep. 29, 2007.
Microwave assisted transesterification of rapeseed oil, Science Direct, by Nezihe Azcan, et al., Dec. 5, 2007.
Mechanisms of Thermochemical Biomass Conversion Processes. Part 1: Reactions of Pyrolysis, Energy Sources, Part A: Recovery, Utilization, and Environmental Effects, by M. Balat, Jan. 1, 2008.
Heterogeneous Catalysts for Biodiesel Production, Energy & Fuels, by Martino Di Serio, et al., Dec. 4, 2007.
Biodiesel Fuel Production by Transesterification of Oils, Journal of Bioscience and Bioengineering, by Nideki Fukuda, et al., Sep. 4, 2001.
The development of a mechanistic model to investigate the impacts of the light dynamics on algal productivity in a Hydraulically Integrated Serial Turbidostat Algal Reactor (HISTAR), Aquacultural Engineering, by Barbara C. Benson, et al., date of publication unknown.
Microalgal Reactors: A Review of Enclosed System Designs and Performances, Biotechnol, by Ana P. Carvalho, et al., 2006.
Isolation and characterization of a novel chytrid species (phylum Blastocladiomycota), parasitic on the green alga *Haematococcus*, Mycological Research, by Yoram Hoffman, et al., 2008.
Photobioreactors for mass cultivation of algae, Bioresource Technology, by C.U. Ugwu, et al., Jan. 31, 2007.
National Algal Biofuels Technical Roadmap Workshop, 4.0 Extraction/Fractionation breakout session, date of publication unknown.
Sub- and supercritical fluid extraction of functional ingredients from different natural sources: Plants, food-by-products, algae and microalgae A review., by Miguel Herrero, et al., Food Chemistry, May 25, 2005.
Evaluation of extraction methods for recovery of fatty acids from lipid-producing microheterotrophs, by Tom Lewis, et al., Journal of Microbiological Methods, Sep. 21, 2000.
Towards more rational techniques for the isolation of valuable essential oils from plants, by M.D. Luque de Castro, et al., 1999.
Effects of harvesting method and growth stage on flocculation of the green alga *Botryococcus braunii*, by S.J. Lee, et al., Letters in Applied Microbiology, Apr. 2, 1998.
Comparison of Centrifugation, Dissolved Air Flotation and Drum Filtration Techniques for Harvesting Sewage-grown Algae, by T.S. Sim, et al., Biomass, Feb. 8, 1988.
Paths toward Algal Genomics, by Arthur R. Grossman, Plant Physiology, Feb. 2005.
Environmental Effects on Cell Composition, by Qiany Hu, publication and date of publication unknown.
10th Deep-Sea Biology Symposium, Sponsor: Oregon Institute of Marine Biology, University of Oregon, Aug. 25-29, 2003.
Vertical Tubular Reactor for Microalgae Cultivation, by K. Miyamoto, et al., Biotechnology Letters vol. 10 No. 10, 1988.
Applications of the deep-shaft activated sludge process in wastewater treatment, by Debabrata Mazumder, et al., Int. J. Environment and Pollution, vol. 17, Nov. 3, 2002.
Biosolids treatment processes, by Lawrence K. Wang, et al., Book, date of publication unknown.
Anaerobe Tolerance to Oxygen and the Potentials of Anaerobic and Aerobic Cocultures for Wastewater Treatment, by M.T. Kato et al., Brazilian Journal of Chemical Engineering, Dec. 1997.
Enhanced Anthocyanin Production from Grape Callus in an Air-Lift Type Bioreactor Using a Viscous Additive-Supplemented Medium, by Hiroyuki Honda, Journal of Bioscience and Bioengineering, May 21, 2002.
Chapter 1—Biological energy production, Deep Shaft & Microbiology prior art, date of publication unknown.
Chapter 2—Energy conversion by photosynthetic organisms, Deep Shaft & Microbiology prior art, date of publication unknown.
Chapter 4—Methane production, Deep Shaft & Microbiology prior art, date of publication unknown.
Chapter 5—Hydrogen production, Deep Shaft & Microbiology prior art, date of publication unknown.
Chapter 6—Oil production, Deep Shaft & Microbiology prior art, date of publication unknown.
Chapter 7—The future of renewable biological energy systems, Deep Shaft & Microbiology prior art, date of publication unknown.
Deep Shaft Process Technology, Industrial, author and date of publication unknown.
Every silver lining has a cloud, The Economist, author unknown, Jan. 29, 2009.
ICI 'Pruteen' plant for manufacturing single cell protein, scienceandsociety.co.uk, author unknown, 1980.
Suspension culture of gametophytes of transgenic kelp in a photobioreactor, by Jiangtao Gao, et al., Biotechnology Letters, May 20, 2005.
Endorsements, Awards & Letters of Recommendation, Vertreat & Vertad, date of publication unknown.
Pulp and Paper Wastewater Treatment (Deep Shaft Process), Japanese Advanced Environment Equipment, author and date of publication unknown.
Smart Economy, Algae bioreactor scrubs CO2 from power plant smokestacks to produce biofuels, Author and date of publication unknown.
The Culture of Coccolithophorid Algae for Carbon Dioxide Bioremediation, by Navid Reza Moheimani—Thesis, 2005.
Activated Sludge Process, NORAM Bio Systems, Inc., date of publication unknown.
Evidence of a Common Pathway of Carbon Dioxide Reduction to Methane in Methanogens, Journal of Baceriology, Jul. 1985, p. 126-131, Jul. 1985.

(56) References Cited

OTHER PUBLICATIONS

Irreversible Climate Change Due to Carbon Dioxide Emissions; Solomon, et al.; 1704-1709, PNAS; Feb. 10, 2009, vol. 106, No. 6.
No to LOHAFEX's Large-Scale Ocean Fertilization Article, Press Release: Antarctic and Southern Ocean Coalition, Jan. 28, 2009.
A Look Back at the U.S. Department of Energy's Aquatic Species Program: Biodiesel from Algae, National Renewable Energy Laboratory, by John Sheehan, et al., Jul. 1998.
Growth and Photosynthesis of Cyanidum Caldarium Cultured Under Pure CO2, Israel Journal of Botany, vol. 20, 1971—pp. 84-90, Seckbach, et al.
The Utilization of a Photobioreactor to Optimize the Growth Rate of Lipids in Microalga for Use in Biofuels, California State Science Fair 2008 Project Summary, by Sarah J. Adams, Apr. 2, 2008.
An SOS Response Induced by High Pressure in *Escherichia coli*, Journal of Bacteriology, by Abram Aertsen, et al., Sep. 2004.
Chemical Profile of Selected Species of Microalgae with Emphasis on Lipids, J. Phycol, by Ami Ben-Amotz, et al., 1985.
Energy Production by Microbial Photosynthesis, Nature, vol. 268, Jul. 7, 1977.
Coastal Biomass From Algae for the Production of Biodiesel, National Renewable Energy Laboratory, pp. 1-18.
Carbon Dioxide Uptake Studies in Algae Grown in Water and Deuterium Oxide, Journal of Pharmaceutical Sciences, Martin I. Blake, et al., Apr. 1962.
Commercial Production of Microalgae: ponds, tanks, tubes and fermenters, Journal of Biotechnology, by Michael A. Borowitzka.
Ultrasound, a new separation technique to harvest microalgae, Journal of Applied Phycology, by Rouke Bosma, et al., 2003.
Conversion of sewage sludge into lipids by Lipomyces starkeyi for biodiesel production, Bioresource Technology, C. Angerbauer, et al., 2007.
Chapter 6—Oil Production, Agriculture and Consumer Protection, FAO Corporate Document Repository, date of publication unknown.
Biodiesel from Microalgae, Biotechnology Advances, by Yusuf Chisti, Feb. 2007.
Extraction of Lipids from Municipal Wastewater Plant Microorganisms for Production of Biodiesel, J. Amer. Oil Chem. Soc., by Stephen Dufreche, et al., 2007.
Effects of Hydrostatic Pressure on Microbial Systems, Bacteriological Reviews, by Carl-Goran Heden, Mar. 1964.
Response of Mediterranean coralline algae to ocean acidification and elevated temperature, Global Change Biology, by Sophie Martin, et al., 2009.
Anaerobic Digestion of Algae, Sanitary Engineering Research Laboratory, Department of Engineering, University of California, Berkeley, California, by C.G. Golueke, et al., Sep. 4, 1956.
Lipids and lipid metabolism in eukaryotic algae, Progress in Lipid Research, by Irina A. Guschina, et al., Jan. 4, 2005.
High-Pressure Microbial Physiology, Department of Microbiology, University of Rochester School of Medicine & Dentistry, by Robert E. Marquis, date of publication unknown.
Investigation of biomass and lipids production with Neochloris oleoabundans in photobioreactor, Bioresource Technology, by J. Pruvost, et al., Jun. 2, 2009.
Deep-Sea Research, Rapid Response Paper, A model of the formation of marine algal flocs by physical coagulation processes, by George A. Jackson, 1990.
Large-scale Continuous Production of Single Cell Protein, Chem.—Eng.—Tech., by Richard Westlake, 1986.
High yield bio-oil production from fast pyrolysis by metabolic controlling of Chlorella protothecoides, Journal of Biotechnology, by Xiaoling Miao, et al., Jan. 16, 2004.
Effects of Hydrostatic Pressure on Marine Microorganisms, Oceanogr. Mar. Biol. Ann. Rev., by Richard Y. Morita, 1967.
Effects of Hypobaric and Hyperbaric Helium Atmospheres on the Growth of Chlorella sorokiniana, Applied Microbiology, by D.M. Orcutt, et al., Jan. 1970.
Lipids and pigments in deep-sea surface sediments and interfacial particles from the Western Crozet Basin, Marine Chemistry, by Laurence Pinturier-Geiss, et al., Mar. 8, 2001.
Pressure pumps up algae biofuel, Energy Research News, author unknown, Apr. 6, 2009.
Publications of Joseph Seckbach, Publications of Science Books, date of publication unknown.
Yeasts in Extreme Environments, Chapter 15, Biotechnical Faculty, by Peter Raspor, et al., date of publication unknown.
The Potential of Microorganisms for Oil Production—A Review of Recent Publications, by Colin Ratledge, Department of Biochemistry, Date of publication unknown.
Growth of Chlorella sorokiniana at Hyperbaric Oxygen Pressures, by B. Richardson, et al., Applied Microbiology, Jan. 1969.
Modeling and Simulation of the Algae to Biodiesel Fuel Cycle, Honors Undergraduate Thesis, by Nick Sazdanoff, Winter 2006.
Survival of Some Fresh-Water Algae Under Extreme Environmental Conditions, by Harold E. Schlichting, Jr., Biocontrol Company, 1974.
Salton Sea finds shares 'gene-jumping' history with its oceanic relatives, by Melody Ward Leslie, Source: EurekAlert!, date of publication unknown.
Microalgae Harvesting and Processing: A Literature Review, A Subcontract Report, Ghelef, et al., Aug. 1984.
Vegetative Life on Venus? or Investigations with Algae Which Grow Under Pure CO2 in Hot Acid Media at Elevated Pressures, by Joseph Seckbach, et al., Institute of Geophysics and Planetary Physics and Department of Chemistry, University of California, Apr. 20, 1970.
Pressure-Induced Color Mutation of Euglena Gracilis; Life Sciences Research Division, IIT Research Institute, Feb. 12, 1965.
Recovery of Biodiesel Precursors from Heterotrophic Microalga Chlorella protothecoides, by Peter B. Merkle, date of publication unknown.
Oil Production Towards Biofuel from Autotrophic Microalgae Semicontinuous Cultivations Monitorized by Flow Cytometry, by Teresa Lopes da Silva, et al., Appl. Biochem. Biotechnol, Nov. 13, 2008.
Small Wonders: biomass from algae, Photobioreactor, by George Marsh, date of publication unknown.
Response of the Photosynthetic Apparatus in *Dunaliella salina* (Green Algae) to Irradiance Stress, by Barbara M. Smith, et al., Plant Physiol., 1990).
Plant Physiology Abstracts; pp. 15-16.
Catalytic gasification of algae in supercritical water for biofuel production and carbon capture, Energy & Enironmental Science, by Samuel Stucki, et al., Feb. 24, 2009.
Gas-Sparged Bioreactors for CO2 Fixation by Dunaliella tertiolecta, by Takahiro Suzuki, et al., J. Chem. Tech. Biotechnol. 1995.
Lipid composition of the nitrogen starved green alga *Neochloris oleoabundans*, by T. G. Tornabene, et al., May 1983.
Biogas Production from Anaerobic Digestion of Spirulina maxima Algal Biomass, Biotechnology and Bioengineering, author unknown, 1982.
Which variety of algae has the highest oil content, Answerbag.com, by Titch98, , Jun. 15, 2008.
Optimization for high-density cultivation of heterotrophic Chlorella based on a hybrid neural network model, by Zhengyun Wu, et al., Letters in Applied Microbiology, 2006.
Biofuels production from Microalgae after heterotrophic growth, by Qingyu Wu, eta I., Department of Biological Sciences and Biotechnology, date of publication unknown.
Chapter 2 unknown—Energy conversion by photosynthetic organisms, Deep Shaft & Microbiology prior art, date of publication unknown.
Chapter 7 unknown—The future of renewable biological energy systems, Deep Shaft & Microbiology prior art, date of publication unknown.
Bill Wilson Environmental Planning, LLC, City Engineer & Public Works Director letter to Clifford Finley, PE, by Bill Wilson, Nov. 27, 2006.

(56) References Cited

OTHER PUBLICATIONS

Microbial Sequestration of Carbon Dioxide and Subsequent conversion to Methane, by Nirupam Pal Associate Professor, California Polytechnic State University, date unknown.
United States Environmental Protection Agency, letter to Dermot O'Brien regarding Jun. 22, 2005 Clean Water Act Inspection, Mar. 10, 2006.
AWWA Water Operator Field Guide, 2d Ed., American Water Works Association (2012), p. 303.

* cited by examiner

DEVICE FOR FUEL AND CHEMICAL PRODUCTION FROM BIOMASS-SEQUESTERED CARBON DIOXIDE AND METHOD THEREFOR

CROSS-REFERENCE TO RELATED APPLICATIONS

This application is a divisional application of Ser. No. 12/661,002, filed Mar. 9, 2010, now U.S. Pat. No. 9,593,300, which claims the benefit of U.S. Provisional Patent Application No. 61/209,929, filed Mar. 12, 2009, and both of which are incorporated herein by reference.

BACKGROUND OF THE INVENTION

Greenhouse gases (GHG) are proven to accumulate in the atmosphere due to manmade sources including burning of fossil fuels. Carbon dioxide ($CO_2$) is implicated as the GHG of most concern by the United Nations and other such organizations, and the buildup of GHG in the atmosphere is possibly linked to rising global temperatures, increasing acidity in the oceans, increased growth of allergic weeds, and other deleterious global-scale problems. Accordingly, there is great interest in development of devices and methods for sequestration of $CO_2$, as well as converting the sequestered carbon to useful materials, such as fuels and chemical products.

SUMMARY OF THE ILLUSTRATED EMBODIMENTS

This invention generally relates to systems, devices and methods of removal and sequestration of $CO_2$ from the atmosphere, flue gases and effluent of industrial facilities, such as but not limited to power plants, landfills, ethanol plants, chemical plants, and the like, by propagation of carbon-sequestering organisms, such as photosynthetic algae, micro algae, cyanobacteria and the like that require light energy, nutrients, water and $CO_2$ to grow organic mass, such as biomass, and/or heterotrophic microorganisms that use chemical carbon, chemical or light energy, nutrients and water to grow organic biomass. The carbon-sequestering biomass generated as a result of carbon sequestration is anaerobically digested to generate methane ($CH_4$). Additionally or alternatively, the additional carbon-sequestering biomass generated can be harvested for use as raw material for biopolymers, bioplastics, biodiesel, and the like, with the extraction waste being anaerobically digested to generate methane.

In a first embodiment, a device for production of methane and chemicals from sequestered carbon is provided. The device include an apparatus for providing a source of carbon; a first processing chamber that is configured and arranged to receive water, the carbon and a biomass, wherein the biomass metabolizes at least a portion of the carbon so as to produce additional biomass; and a second processing chamber that is in fluid flow communication with the first processing chamber, and is configured and arranged for substantial anaerobic digestion at least a portion of the biomass while in the second chamber, such that methane is a digestion product.

In a further embodiment, the device includes a methane collection apparatus associated with the second processing chamber.

In a further embodiment, the device includes a water and nutrient delivery system associated with the first processing chamber.

In a further embodiment, the device includes a carbon dissolving and distributing device for dissolving the carbon in at least one of water flowing into the first processing chamber and water in the first processing chamber.

In a further embodiment, the carbon is carbon dioxide.

In a further embodiment, the carbon is chemical carbon.

In a further embodiment, the biomass is a photosynthetic biomass comprising an organism selected from the group consisting of algae and cyanobacteria.

In a further embodiment, the biomass is a heterotrophic biomass comprising an organism selected from the group consisting of micro-algae, yeast and bacteria.

In a further embodiment, the first processing chamber includes a first zone that is configured and arranged for growth of a photosynthetic biomass and a second zone that is configured and arranged for growth of a heterotrophic biomass. In a still further embodiment, the first and second zones are in fluid flow communication with each other.

In a further embodiment, the first processing chamber is coaxially located within the second processing chamber.

In a further embodiment, the first processing chamber includes an elongated cylindrical shaft having upper and lower ends, and an LED light array located in the shaft. In a still further embodiment, the device includes a mixer located in the shaft. In another further embodiment, the first processing chamber is configured and arranged to subject the biomass to pressure greater than atmospheric pressure. In still another further embodiment, the upper end of the first processing chamber is in fluid flow communication with the second process chamber, such that overflow from the first chamber flows into the second chamber.

In a further embodiment, the second processing chamber includes an elongated cylindrical outer shaft with upper and lower ends, an elongated cylindrical middle shaft with upper and lower ends and that is coaxially located within the outer shaft, and plurality of methanogenic bacteria located therein.

In a further embodiment, a substantial portion of the first and second processing chambers extends vertically into the ground.

In a further embodiment, the biomass is algae and the device includes a light source located in the first processing chamber, where the light source is LEDs having a frequency that tends to promote growth of the algae. In a still further embodiment, the first processing chamber is configured and arranged to subject the algae to a pressure greater than atmospheric pressure.

In a further embodiment, the biomass is a heterotrophic biomass, the carbon source is at least one of organic chemicals, sewage, wastewater, manure and industrial effluent, and the first processing chamber includes an elongated cylindrical shaft having upper and lower ends. In a still further embodiment, the device includes a mixer located in the shaft. In a still further embodiment, the heterotrophic biomass is photosynthetic and the first processing chamber includes a light source having a frequency that tends to promote growth of the heterotrophic biomass.

In a further embodiment, the device includes a physical-chemical treatment apparatus in communication with the first and second processing chambers; wherein the physical-chemical treatment apparatus receives a quantity of biomass from the first processing chamber, processes the received biomass to generate at least one product and a residual biomass; and the second processing chamber receives the residual biomass from the physical-chemical treatment apparatus. In a still further embodiment, the first processing chamber includes a light source; the carbon source is at least one of sewage, waste water, manure, and industrial effluent; and the at least one product is selected from the group consisting of a fermentation substrate, a biopolymer, a bioplastic, an oil, a pigment, a fiber, a protein, a vitamin, a fertilizer and an animal feed. In a still further embodiment, the first processing chamber is configured and arranged to subject to biomass to a pressure greater than atmospheric pressure.

In a second embodiment, a deep well bioreactor is provided for production of methane from carbon dioxide. In this embodiment, the device includes an anaerobic digester, including an elongated outer shaft having upper and lower ends; an elongated middle shaft generally coaxially located within the outer shaft, and having upper and lower ends, wherein the lower end of the middle shaft is in fluid flow communication with the lower end of the outer shaft; a methane collection apparatus in flow communication with upper end of the outer shaft; a plurality of methanogenic microorganisms located within the middle and outer shafts, for substantial anaerobic digestion of a carbon-sequestering biomass, whereby methane is a digestion product; and a biomass incubator generally coaxially located within the middle shaft of the anaerobic digester, the incubator including an elongated cylindrical inner shaft having an interior and upper and lower ends, wherein the upper end of the biomass incubator is in fluid flow communication with the upper end of the middle shaft of the anaerobic digester; a carbon inlet apparatus in communication with the interior of the elongated cylindrical inner shaft, and configured and arranged to provide at least some carbon distribution to water located in the interior of the inner shaft; and a carbon-sequestering biomass located in the interior of the inner shaft, wherein the carbon-sequestering biomass metabolizes at least a portion of the provided carbon so as to produce additional carbon-sequestering biomass, and thereafter the carbon-sequestering biomass is at least partially converted to methane in the anaerobic digester.

In a further embodiment, the device includes at least one of a plurality of LED lights located in the interior of the inner shaft; and a mixer located in the interior of the inner shaft.

In a further embodiment, the biomass incubator further includes a nutrient delivery apparatus in communication with the interior of the inner shaft. In a still further embodiment, the nutrient delivery apparatus includes at least one of a nutrient inlet and a water inlet in fluid communication with the inner shaft. In a still further embodiment, the carbon-sequestering biomass includes a plurality of photosynthetic microorganisms selected from the group consisting of algae and cyanobacteria. In a further embodiment, the device includes a plurality of LED lights that have a frequency that tends to promote growth of the photosynthetic microorganisms.

In a further embodiment, the carbon-sequestering biomass includes a plurality of heterotrophic microorganisms selected from the group consisting of micro-algae, yeast and bacteria.

In a further embodiment, the plurality of methanogenic microorganisms is selected from the group consisting of *Methanosarcina* spp and *Methanothrix* spp.

In a further embodiment, at least a portion of the device is buried and extends vertically into the ground.

In a third embodiment, a method for producing methane from carbon dioxide is provided and includes the steps of exposing a photosynthetic biomass to carbon dioxide, light and nutrients; allowing the photosynthetic biomass to metabolize at least some of the carbon dioxide, whereby additional photosynthetic biomass is produced; thereafter mixing a portion of the photosynthetic biomass with a methanogenic biomass; and allowing the methanogenic biomass to anaerobically digest the portion of the photosynthetic biomass, whereby methane is produced as a digestion product.

In a further embodiment, the method includes collecting the methane produced.

In a further embodiment, the method includes providing water to the photosynthetic biomass.

In a further embodiment, the method includes exposing the photosynthetic biomass to pressure greater than atmospheric pressure.

In a further embodiment, the method includes dissolving carbon dioxide in water and distributing the carbon dioxide-laden water through the photosynthetic biomass.

In a further embodiment, the method includes disposing a plurality of LED lights within the photosynthetic biomass. In a still further embodiment, the method includes exposing the photosynthetic biomass to a pressure greater than atmospheric pressure.

In a further embodiment, the method includes mixing the photosynthetic biomass.

In a further embodiment, the method includes selecting a photosynthetic microorganism selected from the group consisting of algae and cyanobacteria.

In a further embodiment, the method includes flowing the portion of the photosynthetic biomass into the methanogenic biomass.

In a further embodiment, the method includes selecting a methanogenic microorganism from the group consisting of *Methanosarcina* spp and *Methanothrix* spp.

In a further embodiment, the method includes allowing the methanogenic biomass to anaerobically digest the portion of the photosynthetic biomass with a two-phase methane fermentation process, wherein the first phase is acidogenic fermentation and the second phase is methanogenic fermentation.

In a further embodiment, the method includes receiving carbon dioxide from a carbon dioxide source.

In a further embodiment, the method includes growing biomass hydroponically.

In a fourth embodiment, a method for production of methane from carbon dioxide in a deep well bioreactor is provided, including the steps of providing a plurality of methanogenic microorganisms located in an anaerobic digester; providing a carbon-sequestering biomass located in an incubator located coaxially within the anaerobic digester, wherein the incubator is in fluid flow communication with the anaerobic digester; mixing a carbon source with the carbon-sequestering biomass; allowing the carbon-sequestering biomass to metabolize at least a portion of the carbon of the carbon source, whereby additional carbon-sequestering biomass is produced; mixing a portion of the carbon-sequestering biomass with the plurality of methanogenic microorganisms; and allowing the methanogenic microorganisms to substantially anaerobically digest at least a portion of the carbon-sequestering biomass, whereby methane is produced.

In a further embodiment, the method includes providing a plurality of methanogenic microorganisms selected from the group consisting of *Methanosarcina* spp and *Methanothrix* spp.

In a further embodiment, the method includes providing a plurality of carbon-sequestering microorganisms selected from the group consisting of photosynthetic algae, cyanobacteria, heterotrophic micro-algae, yeast and bacteria.

In a further embodiment, the method includes mixing at least one of nutrients and water with the carbon-sequestering biomass.

In a further embodiment, the carbon-sequestering biomass is a photosynthetic biomass; and the method includes comprises exposing the photosynthetic biomass to at least one of visible light and infra red light via a plurality of LEDs located within the incubator. In a still further embodiment, the method includes exposing the photosynthetic biomass to a pressure greater than atmospheric pressure.

In a further embodiment, the method includes flowing the portion of the carbon-sequestering biomass into the plurality of methanogenic microorganisms.

In a further embodiment, the method includes allowing the methanogenic biomass to anaerobically digest the portion of the carbon-sequestering biomass with a two-phase methane fermentation process, wherein the first phase is acidogenic fermentation and the second phase is methanogenic fermentation.

In a further embodiment, the method includes collecting the methane produced.

In a fifth embodiment, a method for producing a product from a carbon-sequestering biomass in a deep well bioreactor is provided, including the steps of providing a source of carbon; incubating the source of carbon with a biomass, wherein the biomass metabolizes at least a portion of the carbon of the carbon source so as to produce additional biomass; and subjecting at least a portion of the biomass to physical-chemical treatment, so as to produce a product selected from the group consisting of a fermentation substrate, a biopolymer, a bioplastic, an oil, a pigment, a fiber, a protein, a vitamin, a fertilizer and an animal feed.

In a further embodiment, the method includes providing a carbon source selected from the group consisting of organic chemicals, sewage, wastewater, manure and industrial effluent; and providing a heterotrophic biomass.

In a further embodiment, the method includes providing a carbon source including carbon dioxide, and providing a light source; and providing a photosynthetic biomass.

Some of the advantages of the present invention over the prior art include the following. The illustrated device and described methods remove $CO_2$, a major greenhouse gas and an air pollutant, from any $CO_2$ laden air stream, such as atmospheric air, combustion gases of power plants, land fill gases, and the like, and transforms the $CO_2$ into a photosynthetic biomass. Removal of the $CO_2$ is maximized by utilizing a deep well reactor, such as a bioreactor, which increases the solubility of the $CO_2$ because of the higher temperature and pressure associated with deep well reactors. LED lights are used to provide consistent and controlled frequencies of visible and infra red light, whereby maximum photosynthetic and growth rates can be achieved in return for the energy utilized to provide light. Furthermore, the illustrated device and methods advantageously remove chemical carbon from effluents using a heterotrophic biomass, and transforms the chemical carbon into methane. Incidental metals are also removed from industrial and/or ground waters, when they are used as an influent to the photosynthetic reactor by means of adsorption to the biomass. Furthermore, by configuring the device as a deep well reactor, land requirements are substantially reduced relative to the land requirements of above-ground systems. Additionally, separation of algae biomass from the liquid is made easier by using the dissolved air flotation process. When the suspension is drawn from the deep well, pressure is released, thereby causing air bubbles to come to the surface. The biomass attaches to the air and rises to the surface, enhancing the liquid-solid separation.

Useful products are generated by the illustrated embodiments. For example, methane ($CH_4$), which can be used to generate energy and/or as a raw material, is generated by anaerobic digestion of the carbon-sequestering biomass. In another example, at least a portion of the carbon-sequestering biomass can be recovered and used for raw materials, such as fiber, animal feed, and fertilizer, organic chemicals, such as recovered oils, purified substances such as nutrients, vitamins, biopolymers and bioplastics, and pigments, and/or an industrial feedstock, such as fermentation substrate. Conversion of $CO_2$ into methane is enhanced due to the recirculation of a portion of the generated biogas into the digestion liquor. Due to the high pressure, such as pressure greater than atmospheric pressure, in the deep well reactor, solubility of $CO_2$ in the digestion liquor is increased and more $CO_2$ is converted to methane by anaerobic bacteria. Furthermore, Certified Emission Reductions (CERs) are generated, which can be traded on global carbon exchange markets, as determined by the Kyoto Protocol and pending climate change conventions and agreements.

Various objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

Figure 1:
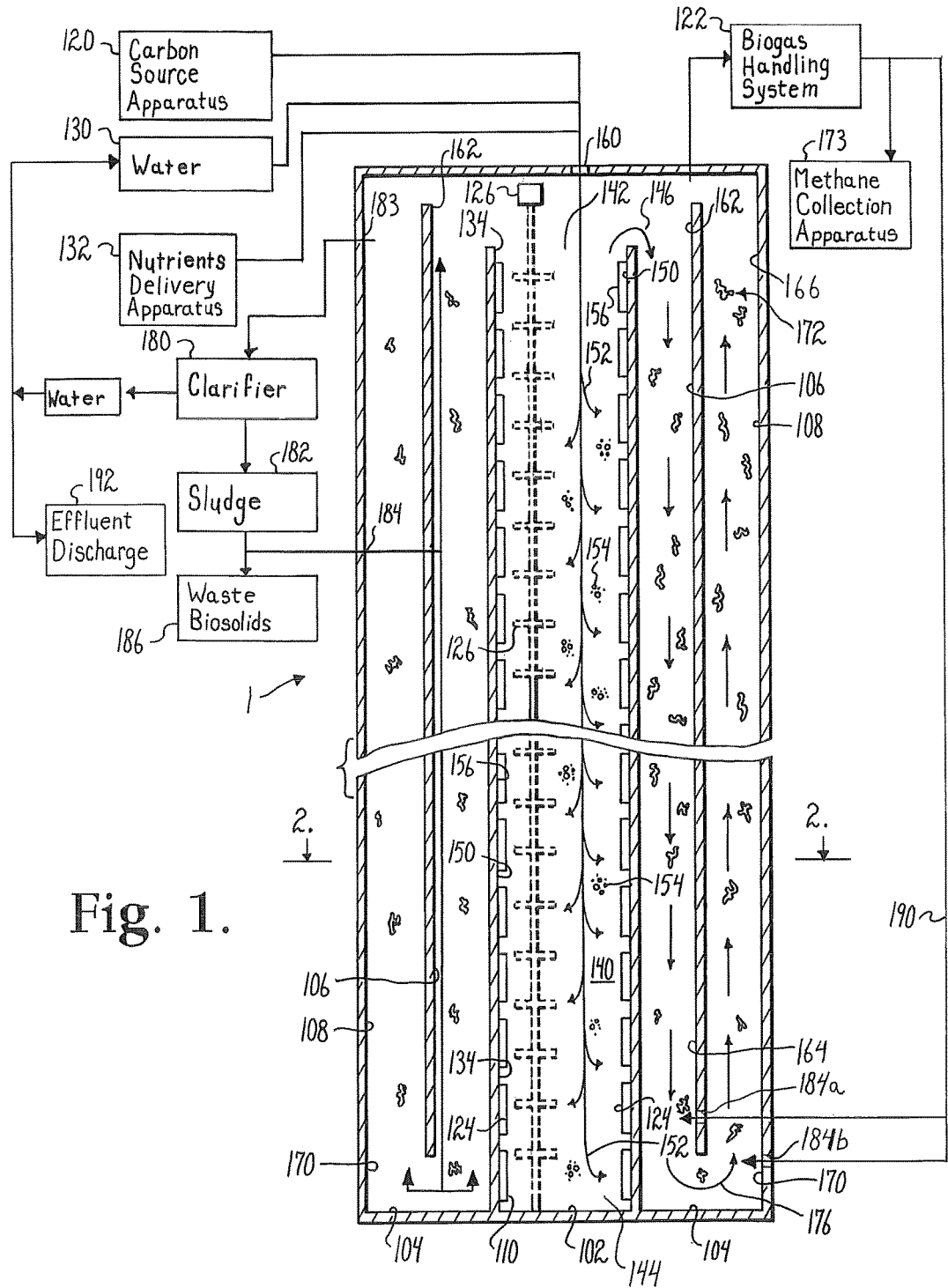
FIG. 1 is a partially schematic drawing of a deep well bioreactor for carbon sequestration and methane production with portions exposed to show detail thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

In the illustrated embodiments, production of methane from a carbon source is accomplished in two stages, such as processes or steps. In some embodiments, the carbon source is $CO_2$, such as is found in atmospheric gases, flue gases, and the like. In some embodiments, the carbon source is chemical carbon. Suitable chemical carbon sources include but are not limited to organic chemicals, sewage, waste water, manure, and industrial effluent.

In the first stage, carbon, such as $CO_2$ or chemical carbon, is sequestered in carbon-sequestering microorganisms. In circumstances wherein the carbon source is $CO_2$, the carbon-sequestering microorganisms are generally photosynthetic, such as algae, micro algae, cyanobacteria, hydroponic plants or plant fragments and the like. Such photosynthetic microorganisms metabolize the $CO_2$, such as in the presence of light energy, and multiply or grow and increase the biomass, such as biological material derived from living, or recently living organisms, especially micro- or macro-algae, bacteria, yeast, and callus, or higher plants that can be grown individually in a hydroponic state, thereby generating or producing additional photosynthetic microorganisms, such that the biomass is expanded. In circumstances wherein the carbon source is chemical carbon, the carbon-sequestering microorganisms are heterotrophic, and may or may not be photosynthetic. The heterotrophic microorganisms metabolize the chemical carbon and multiply and increase the carbon-sequestering biomass, thereby generating additional heterotrophic microorganisms. Useful heterotrophs include but are not limited to micro-algae, such as *Chlorella protothecoides, Euglena gracilis, Cyclotella cryptica, Monoraphidium minutum*, yeast, such as *Sacchromycese cerevisiae*, and bacteria, such as *Bacillus subtilis*.

In some embodiments, in the second stage, the sequestered carbon is converted into methane when at least some of the carbon-sequestering microorganisms of the first stage, such as a portion of the expanded biomass, are anaerobically digested, such as by a two-phase process, wherein acidogenic fermentation is the first phase and methanogenic fermentation is the second phase, to produce methane. It is foreseen that other microorganism driven processes, of types well known in the digestion industry, could be utilized to produce methane from the biomass. Both stages, such as carbon sequestration and methane generation, take place in a generally vertical, circular, deep well, underground bioreactor, such as described herein.

In some embodiments, prior to the second stage, at least a portion of the carbon-sequestering biomass is processed using physical-chemical processes, to produce chemicals, such as but not limited to fermentation substrates, biopolymers, bioplastics, oils, pigments, fiber, proteins, vitamins, fertilizer, and animal feed, such as described below. A residue, generated by the physical-chemical processes, is subjected to the second stage, to produce methane from the residue.

Figure 2:
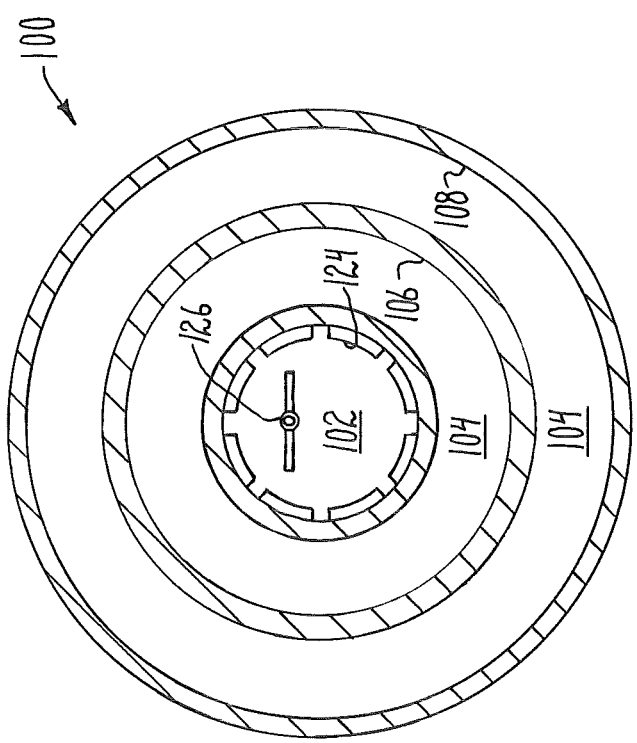
FIG. 2 is a cross section of the bioreactor, taken along line 2-2 of FIG. 1.

FIGS. 1-2 illustrate a first embodiment of a device 100 for producing methane from a carbon source, such as but not limited to $CO_2$ and chemical carbon. The device includes a first processing chamber 102, such as an incubator, reactor, bioreactor, inner chamber, photo bioreactor, referred to herein as a carbon-sequestering biomass incubator, and a second processing chamber 104, such as an incubator, reactor, bioreactor, and referred to herein as an anaerobic digester, that includes a middle chamber 106 and an outer chamber 108. The carbon-sequestering biomass incubator 102 is in fluid flow communication with the anaerobic digester 104. For example, at least some of the fluid in the carbon-sequestering biomass incubator 102 flows into the anaerobic digester 104. The device also includes a carbon source inlet apparatus 120 for supplying, delivering and/or distributing carbon to the carbon-sequestering biomass incubator 102, a collection apparatus 122, such as methane collection apparatus, biogas handling system, for collecting the methane product from the anaerobic digester 104, an optional light source 124 located within the first processing chamber 102, and an optional mixing apparatus 126 (shown in phantom) also located within the first processing chamber 102.

At least a portion of the device 100 extends below the ground. In preferred embodiments, a substantial portion of the device 100, such as a substantial portion of the carbon-sequestering biomass incubator 102 and of the anaerobic digester 104, extends generally vertically into the ground. Extending the device below ground level increases the pressure within the under-ground portion of the device to a pressure greater than atmospheric pressure (at ground level). Advantageously, higher pressures increase the solubility of the $CO_2$ in the fluid. Consequently, when under pressure, the increased $CO_2$ concentration increases the rate of sequestration, such as by the photosynthetic microorganisms, and additionally or alternatively increases the rate of conversion of the sequestered CO2 to methane. In some embodiments, at least a portion of the device 100 extends from between about 50, 100, 200, 300, 400, 500, 600, 700, 800, 900, and 1000 meters and about 1100, 1200, 1300, 1400, 1500, 1600, 1700, 1800, 1900, and 2000 meters or more into the ground. In some embodiments, the device 100 extends from between about 0.25, 0.5, 0.75, and 1.0 miles and about 1.25, 1.5, and 1.75 miles or more into the ground. Additionally, the device 100 includes an inner reactor, such as the carbon-sequestering biomass incubator 102, and an outer reactor, such as the anaerobic digester 104. In some embodiments, the inner reactor 102 has a diameter of from between about 1, 2, 3, or 4 feet and about 6, 7, 8 or 9 feet or more. In some embodiments, the outer reactor 104 has a diameter of from between about 10, 11, 12 or 13 feet and about 14, 15, 16, 17 or 18 feet or more.

In some embodiments, the carbon-sequestering biomass incubator 102, such as the first processing chamber or first reactor 102 is a photo bioreactor, such as for the incubation, growth and/or expansion of a photosynthetic carbon-sequestering organism, such as an algae or cyanobacterium, or optionally a photosynthetic heterotroph. A variety of algae and cyanobacterium known in the art can be used, such as described herein. In this embodiment, the carbon-sequestering biomass incubator 102 includes a light source 124, discussed in greater detail below, and is configured and arranged to receive one or more influents. Influents received by the first chamber include at least one of, but not limited to, water 130 ($H_2O$), nutrients 132, and a source of carbon, such as but not limited to $CO_2$ dissolved in water by an apparatus 120 configured therefor, such as a $CO_2$ source apparatus, $CO_2$ inlet apparatus. In a further embodiment, the carbon-sequestering biomass incubator 102 subjects the photosynthetic, carbon-sequestering biomass therein to increased pressure, such as a pressure greater than atmospheric pressure at ground level, in the presence of light 124.

In some embodiments, the carbon-sequestering biomass incubator 102, such as the first processing chamber or a first reactor 102, is a heterotrophic bioreactor, such as for the incubation, growth and/or expansion of a heterotrophic carbon-sequestering organism. In circumstances in which the carbon-sequestering biomass includes heterotrophs, the carbon source is chemical carbon, such as described elsewhere herein. In this embodiment, the carbon-sequestering biomass incubator 102 may include a light source 124, such as for photosynthetic heterotrophs, and is configured and arranged to receive one or more influents. Influents received by the first chamber include at least one of, but not limited to, water 130 ($H_2O$), nutrients 132, and a source of carbon, such as but not limited to chemical carbon dissolved in water by an apparatus 120 configured therefor, such as the carbon source apparatus or a carbon inlet apparatus. In a further embodiment, the carbon-sequestering biomass incubator 102 subjects the heterotrophic, carbon-sequestering biomass therein to increased pressure, such as a pressure greater than atmospheric pressure at ground level. In some embodiments, the heterotrophic biomass is also photosynthetic, and the incubator 102 includes a suitable light source to increase or promote growth of the biomass.

Upon initial use, or first start up, of the device 100, the carbon-sequestering biomass incubator 102 receives an innoculum, or initial culture, of a suitable carbon-sequestering biomass, such as the algae, cyanobacterium, or heterotrophic microorganism. During device operation, the carbon-sequestering biomass metabolizes at least a portion of the carbon received, such as an influent, so as to produce additional carbon-sequestering biomass, or the biomass expands, grows or multiplies, which is then used to generate methane in the anaerobic digester 104, such as the second processing chamber. In some circumstances, a portion of the carbon-sequestering biomass is harvested for use as raw materials, such as fiber, animal feed and/or fertilizer, for production of organic chemicals, such as recovered oils, purified substances such as nutrients, vitamins, biopolymers and bioplastics, and pigments, and for industrial feedstock, such as a fermentation substrate, and as describe below, with reference to FIG. 4.

The carbon-sequestering biomass incubator 102 is generally coaxially located within the middle shaft 106, such as the middle chamber, mixing chamber or shaft, of the anaerobic digester 104. As shown in FIG. 1, the carbon-sequestering biomass incubator 102 is an elongated cylindrical inner shaft 134 having an interior 140, an upper end 142 and a lower end 144. The upper end 142 of the carbon-sequestering biomass incubator 102 is open, such that a portion 146 of the carbon-sequestering biomass therein can flow out, such as by 146, of the upper end 142, such as over the shaft's side wall 150, and into the middle shaft 106, such as the middle chamber, of the anaerobic digester 104.

A carbon inlet apparatus 152, such as the $CO_2$ inlet apparatus 152, is associated with and in communication with the interior 140 of the carbon-sequestering biomass incubator 102, such as the elongated cylindrical inner shaft. The carbon inlet apparatus 152 is configured and arranged to provide at least some carbon, such as $CO_2$ or chemical carbon, distribution to water located in the interior of the elongated shaft. For example, the carbon inlet apparatus 125 can include $CO_2$ gas diffusers, jet nozzles, spargers, bubblers, educators, injectors and the like that are spaced along the length of the carbon-sequestering biomass incubator 102 and deliver, or expel or inject, gaseous $CO_2$ 154, or gaseous or liquid chemical carbon, into the water, such as the liquor containing the biomass, within the interior 140 of the carbon-sequestering biomass incubator 102, such that at least some of the carbon, such as $CO_2$ 154, becomes dissolved therein. It is noted that for convenience, in the Figures $CO_2$ 154 represents both $CO_2$ and chemical carbon. It is foreseen that the carbon can also be carried by, or mixed with, water 130 entering the incubator 102 or supplemented thereby. For example, chemical carbon-laden sewage can be mixed with, or diluted with, water entering the incubator 102. Suitable sources of $CO_2$, such as a $CO_2$-laden air stream, include but are not limited to atmospheric air, combustion gases of power plants and manufacturing plants, land fill gases, and the like. Suitable sources of chemical carbon include but are not limited to organic chemicals, sewage, waste water, manure and industrial effluent.

In a further example, a plurality of spargers 154, such as is known in the art, are spaced along the length of the carbon-sequestering biomass incubator's interior 140 and inject a controlled amount of carbon, such as $CO_2$ laden air, as gaseous or liquid chemical carbon, into the culture of algae, cyanobacteria or other biomass. Some of the carbon, such as depicted as $CO_2$ 154, dissolves into or mixes with the culture media, such as water with nutrients, such as but not limited to nitrogen, phosphorus, and micronutrients therein. Some of the $CO_2$ 154 forms bubbles that rise to the surface and thereby generate a mixing action of the culture.

In some embodiments, the device 100 includes an optional mixing apparatus 126, located in the interior 140 of the carbon-sequestering biomass incubator 102, to facilitate mixing of the algal or bacterial culture (described in greater detail below). It is foreseen that mixing can be provided by other devices that are well known in the art such as circulating pump systems, flow diverters, incoming fluid spargers, jet nozzles, educators, pulse air mixers, paddles, and the like. While not wishing to be bound by theory, it is believed that carbon removal, especially $CO_2$ removal, and methane production is maximized by the dynamics of a deep well reactor, which increases the solubility of the carbon, such as $CO_2$, due to the higher pressure, or pressure greater than atmospheric pressure, and higher temperature within the deep well reactor.

The carbon inlet apparatus 152 injects the carbon into the interior 140 of the carbon-sequestering biomass incubator 102. For example, a $CO_2$ inlet apparatus 152 dissolves $CO_2$ 154 into a stream of water 130, that is injected, such as flows, is delivered or provided to, into the interior 140 of the carbon-sequestering biomass incubator 102. In another example, a chemical carbon inlet apparatus 152 mixed liquid effluents, such as from a manufacturing plant, with the water stream 130, that is injected, such as flows, is delivered or provided to, into the interior 140 of the carbon-sequestering biomass incubator 102. The carbon can be injected near, at or adjacent to the bottom 144 of the elongated inner shaft or inner chamber, or at any location along the length of the shaft. For example, the carbon can be injected at a location, such as within the shaft, from about 10%, 20%, 30%, 40% or 50% of the shafts length, with respect to the top end 142 of the shaft, to about 60%, 70%, 90%, 85%, 90% or 95% of the shafts length or at evenly or unevenly spaced locations therealong. Nutrients 132 can be added to the carbon, such as by a nutrient delivery apparatus, prior to injection. Injection of the carbon can also provide a mixing action to the carbon-sequestering biomass culture.

A photon source is required to drive photosynthesis in photosynthetic organisms. Accordingly, in some embodiments, the carbon-sequestering biomass incubator 102 includes a light source 124 sufficient for photosynthesis by a photosynthetic carbon-sequestering biomass. In some embodiments, constant and controlled frequencies of visible and infra red light are made available to a photosynthetic biomass via a plurality of LED lights 124, such as an LED light array, located in the interior 140 of the elongated cylindrical shaft 134, such as the inner shaft. For example, a plurality of LED lights 124 can extend the length of the inner processing chamber 140. In a further example, strings of LEDs 124, such as LEDs attached to electrical wires, can be hung or suspended within the inner chamber 134, such as a drop down, removable array of LED lights. In another example, LEDs can be attached to the sides 156 or walls of the chamber 134. The LEDs can be spaced along the length of the chamber 134, either singly or in clusters. In yet another example, strings of LEDs are suspended within the interior 140 of the chamber 134 and LEDs are attached to the sides 156 of the chamber 134. In another example, the light source 124 includes fiber optics. The light source 124 is configured and arranged to provide visible light and optionally infra red light, such that the photosynthetic microorganisms can perform photosynthesis. It is noted that such LED lights are flashed on and off, in order to reduce energy consumption and to protect the photosynthesis from exhaustion. In preferred embodiments, the photosynthetic organisms receive an amount to light for sufficient photosynthesis for an extended period of time, whereby carbon sequestration by the photosynthetic carbon-sequestering microorganisms is maximized.

An optional mixing apparatus 126 may be located in the interior 140 of the carbon-sequestering biomass incubator 102, such as within the inner chamber 136, whereby the liquor in this chamber is continuously mixed and the biomass is kept in suspension. The mixing apparatus 124 includes one or more mixing devices know in the art, such as but not limited to circulating pump systems, flow diverters, incoming fluid spargers, jet nozzles, educators, pulse air mixers, paddles, and the like. The mixing devices are spaced along the length of the chamber 136, such that exposure of the microorganisms to light and nutrients is optimized for maximal carbon sequestration and the microorganisms, or biomass, are suspended in the liquor. A portion of the suspended carbon-sequestering microorganisms, such as algae, cyanobacteria or other biomass, overflow 146, such as at the surface of the first chamber 102 or over wall 150, into the anaerobic digester 104.

A nutrient delivery apparatus 132 is associated with carbon-sequestering biomass incubator 102, such as the inner shaft. In some embodiments, the nutrient delivery apparatus 132 includes at least one of a nutrient inlet 174 and a water inlet 160 in fluid communication with the carbon-sequestering biomass incubator 102, such as the interior chamber 134. For example, the nutrient deliver apparatus 132 can include one or more nozzles or valves located along the length of the carbon-sequestering biomass incubator 102, for the injection or delivery, such as inflow, of a nutrient-bearing water stream or culture medium. Incidental removal of metals or other contaminants can be achieved if metal or contaminant-bearing water, such as the water 130, is used as an influent, generally by absorption of the metal/contaminant onto the carbon-sequestering biomass. Injection of the nutrients can assist in liquor mixing. For example, a nozzle or optionally mixer 126, shown in phantom, can be pointed generally downward, such as vertically with respect to the inner shaft 134, or sideways, such as horizontally with respect to the shaft 134, to create a local vortex or turbulence, for increased mixing at that location. In another example, a nozzle is pointed upward, to assist in a general upflow of the liquor.

The anaerobic digester 104, such as the second process chamber or outer reactor, is configured and arranged similarly to deep well bioreactors known in the art, such as but not limited to "VERTREAT" and "VERTAD" type bioreactors described in U.S. Pat. Nos. 5,650,070 and 6,468,429 to Pollock and U.S. Pat. No. 4,217,211 to Crane, all of which are incorporated herein by reference. The anaerobic digester 104 includes an elongated cylindrical middle chamber 106, such as a middle shaft or mixing shaft, having upper and lower ends 162, 164 and an elongated cylindrical outer shaft 108 having upper and lower ends 108a, 170, and plurality of methanogenic bacteria 172, such as methanogenic biomass, located therein. The anaerobic digester 104 is configured and arranged such that the methanogenic biomass 172 can circulate therethrough while receiving a portion of the carbon-sequestering biomass, such as overflowing from the carbon-sequestering biomass incubator 102. The middle shaft 106, such as the middle chamber or mixing shaft, is generally coaxially located within the outer shaft 108, such as the outer chamber, and the carbon-sequestering biomass incubator 102 is generally coaxially located within the middle shaft 106, such that overflow from the carbon-sequestering biomass incubator 102 into the second chamber 104, such as into the middle shaft 106. The top ends 162, 166 of the middle and outer shafts 106, 108 are in fluid flow communication with each other, such as open to each other. Similarly, bottom ends 164, 170 of the middle and outer shafts 106, 108 are in fluid flow communication with each other or open to each other. The methanogenic microorganisms 172 located within the middle and outer shafts 106, 108, such as the anaerobic digester 104, substantially anaerobically digest the carbon-sequestering biomass that flows into the anaerobic digester 104, whereby methane ($CH_4$) is a digestion product.

U.S. Pat. No. 4,217,211 provides, in a deep well treatment of sewage, an apparatus having an outer elongated shaft, said outer shaft having an upper end and a lower end, said upper end being located at or near the earth's surface and said lower end being located at a subterranean level. The outer shaft descends from the earth's surface downwardly for a suitable distance, as hereinafter described, defining the subterranean shaft. In one instance, U.S. Pat. No. 4,217,211 mentions that hydrostatic pressure within the subterranean shaft reaches 80 psi at a depth slightly below 200 feet (approximately 61 meters). In a preferred construction, the subterranean shaft would extend down into the earth for at least 750 feet (approximately 229 meters).

The top end 162 of the middle shaft 106, such as the mixing chamber, is open to the carbon-sequestering biomass incubator 102, and a portion of the liquor in the carbon-sequestering biomass incubator 102, which contains some carbon-sequestering microorganisms, overflows 146 into the middle shaft 106. The top end 162 is also open to the top end 166 of the outer shaft 108, such as the outer chamber, but fluid flowing from the outer shaft 108 and into the top end 162 of the middle shaft 106 does not substantially flow into the carbon-sequestering biomass incubator 102. The liquor from the outer shaft 108 discharges through an outlet 174.

While in the middle shaft 106 of the anaerobic digester 104, the carbon-sequestering biomass, such as from the biomass incubator 102, undergoes the first phase of anaerobic digestion, stage, step or process, known as the acetogenic phase or acetogenic fermentation. During the acetogenic phase, enzymes secreted by certain bacteria, such as *Bacteroides, Butyrivibrio, Clostridium, Fusobacterium, Selonomonas, Peptococcus, Streptococcus*, and the like, present in the liquor digest the algae, cyanobacteria or other biomass, such as proteins, lipids and carbohydrates therein, and generate acetate. In preferred embodiments, the acetogenic phase is carried out under substantially anaerobic conditions, using anaerobic bacteria.

The bottom end 164 of the middle shaft 106 is open to the bottom end 170 of the outer shaft 108, and liquor in the middle shaft 106 flows 176, such as by underflow, into the outer shaft 108 and then in a generally upward direction, toward the top end 166 of the outer shaft 108. While in the outer chamber 108, the effluent from the middle shaft 106 undergoes the second phase of anaerobic digestion, called the methanogenic phase. Under anaerobic conditions, methanogenic bacteria 172, such as methanogens, *Methanosarcina* spp. and/or *Methanothrix* spp. present in the digestion liquor convert the acetate ($CH_3COOH$) into methane ($CH_4$). In general, the methanogens consume hydrogen ($H_2$) and $CO_2$, and reduce $CO_2$ as an electron accentor via the formyl, methenyl, and methyl levels through association with coenzymes, to finally produce methane ($CH_4$). The overall reaction can be expressed as: $CH_3COOH \rightarrow CH_4 + CO_2$. The resulting methane 173 is captured by a methane capture device 122, such as a biogas handling system or a methane collection apparatus, associated with the second processing chamber 104, such as is associated with the top end 170 of the outer shaft 108.

The treated effluent from the outer chamber 108 is generally removed into an above ground dissolved air flotation unit, such as a clarifier 180, where the biomass is separated from the liquor. A portion of the concentrated biomass, such as sludge 182, is recirculated towards the bottom 164 of the middle shaft 106, such as by an inlet 184, so as to provide a starting culture of acetogenic and methanogenic bacteria. The excess collected biomass or waste biosolids 186, such as from the anaerobic digester 104, is disposed of using methods known in the art, such as in fertilizer, burned for power, and the like. The biogas produced during the digestion process is collected above ground, such as by the methane collection apparatus 122, and a portion 190 of the biogas is recirculated to both the middle and outer shafts 106, 108, to promote mixing and to increase the solubility of $CO_2$ in the digestion liquor. In some embodiments, hydrogen ($H_2$) is also added, to increase conversion of the carbon-sequestering biomass into methane. While not wishing to be bound by theory, it is believed that conversion of the $CO_2$ in the biogas into methane, such as causing a higher proportion of methane content in the biogas, is enhanced by the recirculation of a portion 190 of the biogas into the digestion liquor, due to the high pressure in the deep well reactor, such as solubility of $CO_2$ in the digestion liquor is increased and more $CO_2$ is converted to methane by the anaerobic bacteria.

Figure 3:
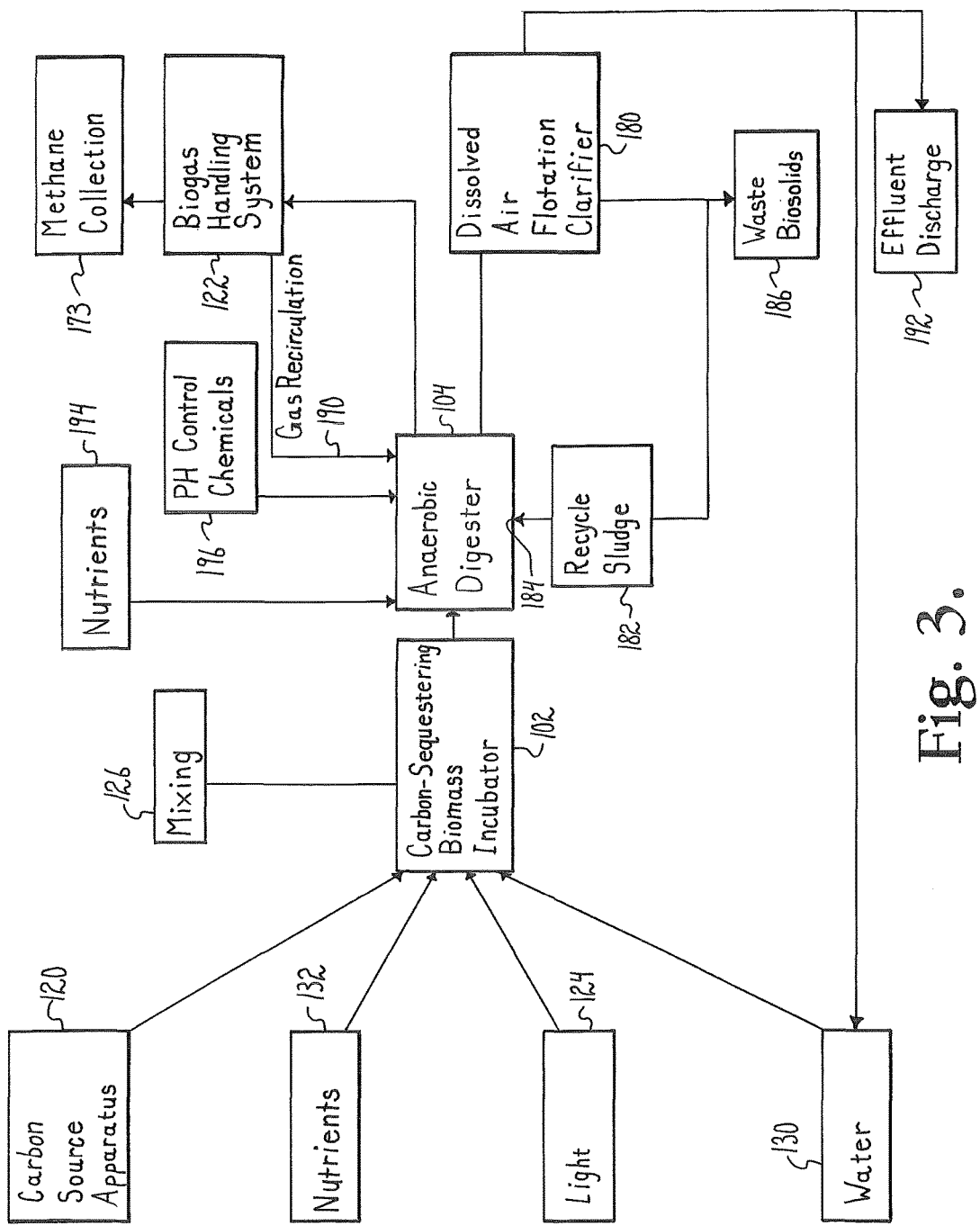
FIG. 3 is a flow diagram of the inputs and output of a method for carbon sequestration and methane production in a deep well bioreactor.

FIG. 3 illustrates a method of using the device of the illustrated embodiments, namely a method for producing methane from a carbon source such as $CO_2$ or chemical carbon. In general, a device 100 of the illustrated embodiments is provided. This includes providing a plurality of methanogenic microorganisms 172 located in an anaerobic digester 104 and providing a carbon-sequestering biomass located in an incubator, such as carbon-sequestering biomass incubator 102, that is located coaxially within the anaerobic digester 104, wherein the incubator 102 is in fluid flow communication with the anaerobic digester 104. In some embodiments, the plurality of methanogenic microorganisms 172 provided is selected from the group consisting of *Methanosarcina* spp and *Methanothrix* spp. In some embodiments, the plurality of photosynthetic microorganisms provided is selected from the group consisting of algae and cyanobacteria. It is foreseen that the carbon sequestration and anaerobic digestion of sequestered biomass can also be achieved in above-ground high pressure reactors simulating deep well reactor conditions. It is foreseen that the carbon sequestration and anaerobic digestion of the sequestered biomass can also be achieved in horizontal deep tunnels as in vertical deep wells.

Carbon, such as a $CO_2$-laden air stream or a liquid chemical carbon stream, is mixed with the carbon-sequestering biomass. The carbon is received from a carbon source, such as the apparatus 120, such as by injection through a carbon inlet apparatus 152 or the like. For example, the $CO_2$-laden air stream 120 can be derived from atmospheric air, flue gases, such as from power plants or manufacturers, and landfill gases. Additional influents, or inputs, include but are not limited to nutrients 132, water 130 and light 124. Water 130 can be supplied from a variety of sources, such as but not limited to freshwater, waste water, sea water, and ground water. In some embodiments, the carbon-sequestering biomass is photosynthetic and constant and controlled light 124 are provided, such as by LEDs and/or fiberoptics. Alternatively or additionally, in some embodiments, the carbon-sequestering biomass is subjected to a pressures that is greater that atmospheric pressure at ground level. The contents of the deep well carbon-sequestering bioreactor is mixed.

In another step of the method of the illustrated embodiment, the carbon-sequestering biomass is allowed to metabolize at least a portion of the carbon, whereby additional carbon-sequestering biomass is produced, such as the photosynthetic biomass grows, increases or expands.

Next, a portion of the carbon-sequestering biomass is mixed with the plurality of methanogenic microorganisms in the anaerobic digester 104. For example, the portion of the carbon-sequestering biomass can flow, see FIG. 1, 146, into the plurality of methanogenic microorganisms 172, such as a methanogenic biomass, whereby the two biomasses become mixed or combined. One or more inputs can be added to the anaerobic digester 104. For example, additional nutrients 194 and/or pH control chemicals 196 can be added to the anaerobic digester 104, either continuously or on an as-needed basis. An amount of biogas 190 can be added, or recirculated or recycled, such as to enhance mixing and to promote $CO_2$ conversion into methane, as described elsewhere herein. An amount of recycled sludge 182, such as from effluent, can be added to the anaerobic digester 104, to replenish the methanogenic microorganisms 172.

The methanogenic microorganisms 172 are allowed to substantially anaerobically digest the portion of the carbon-sequestering biomass mixed therein, whereby methane 173 is produced, such as a digestion product. Namely, the methanogenic biomass 172 is allowed to anaerobically digest the portion of the carbon-sequestering biomass with a two-phase methane fermentation process, wherein the first phase is acidogenic fermentation and the second phase is methanogenic fermentation, such as described elsewhere herein. As described elsewhere herein, in some embodiments, the methanogenic fermentation occurs at a pressure greater than atmospheric pressure at ground level.

The methane 173 is contained in biogas, which is directed into a biogas handling system, such as the methane collection apparatus 122. The methane 173 produced is collected, or separated from the biogas, by the methane collection apparatus 122. A portion 190 of the biogas is returned or recycled to the anaerobic digester 104. While not wishing to be bound by theory, it is believed that higher $CO_2$ concentrations promote conversion of acetate to methane by the methanogenic bacteria 172.

A variety of photosynthetic algae can be used with the present invention, such as but not limited to *Macrocystis*, such as *Macrocystis angustifolia, Macrocystis integrifolia, Macrocystis laevis*, and *Macrocystis pyrifera*, and *Microcystis*. While algae and cyanobacteria, also known as blue-green algae, blue-green bacteria or *Cyanophyta*, are useful in the present invention, it is foreseen that micro algae, such as *Astaxinthin, Chlorella, Spirulina, Volvox, Prochlorococcus, Calothrix*, and the like, could be utilized as well as hydroponically grown plants or plant fragments, or plant calli, such as a continuous plant cell culture. Further, some algae that sequester carbon as calcium carbonate are useful in the present invention. These algae include, but are not limited to, *Turbinaria ornata* and *Emiliania huxleyi*. In some embodiments, the photosynthetic biomass is grown hydroponically using methods known in the art.

A variety of heterotrophic microorganisms can be used with the present invention, including but not limited to micro-algae, such as *Chlorella protothecoides, Euglena gracilis, Cyclotella cryptica, Monoraphidium minutum*, yeast, such as *Sacchromycese cerevisiae*, and bacteria, such as *Bacillus subtilis*.

A portion of the digestion liquor is collected in, or flows into or is diverted into, a dissolved air flotation device, such as the clarifier 180. The dissolved air flotation device separates the methanogenic biomass, a portion of which, such as the sludge 182, is recycled to the anaerobic digester 104, such as by the inlet 184. The remaining methanogenic biomass is disposed of as waste 186, such as biosolids. A final liquid effluent 192, such as water, is produced, which can be evaporated or disposed of as liquid waste using methods known in the art. Additionally, a portion of the effluent water 192 can be recycled back to the carbon-sequestering biomass incubator 102 and/or to the anaerobic digester 106, as the effluent water 192 contains nutrients from the digestion process.

Figure 4:
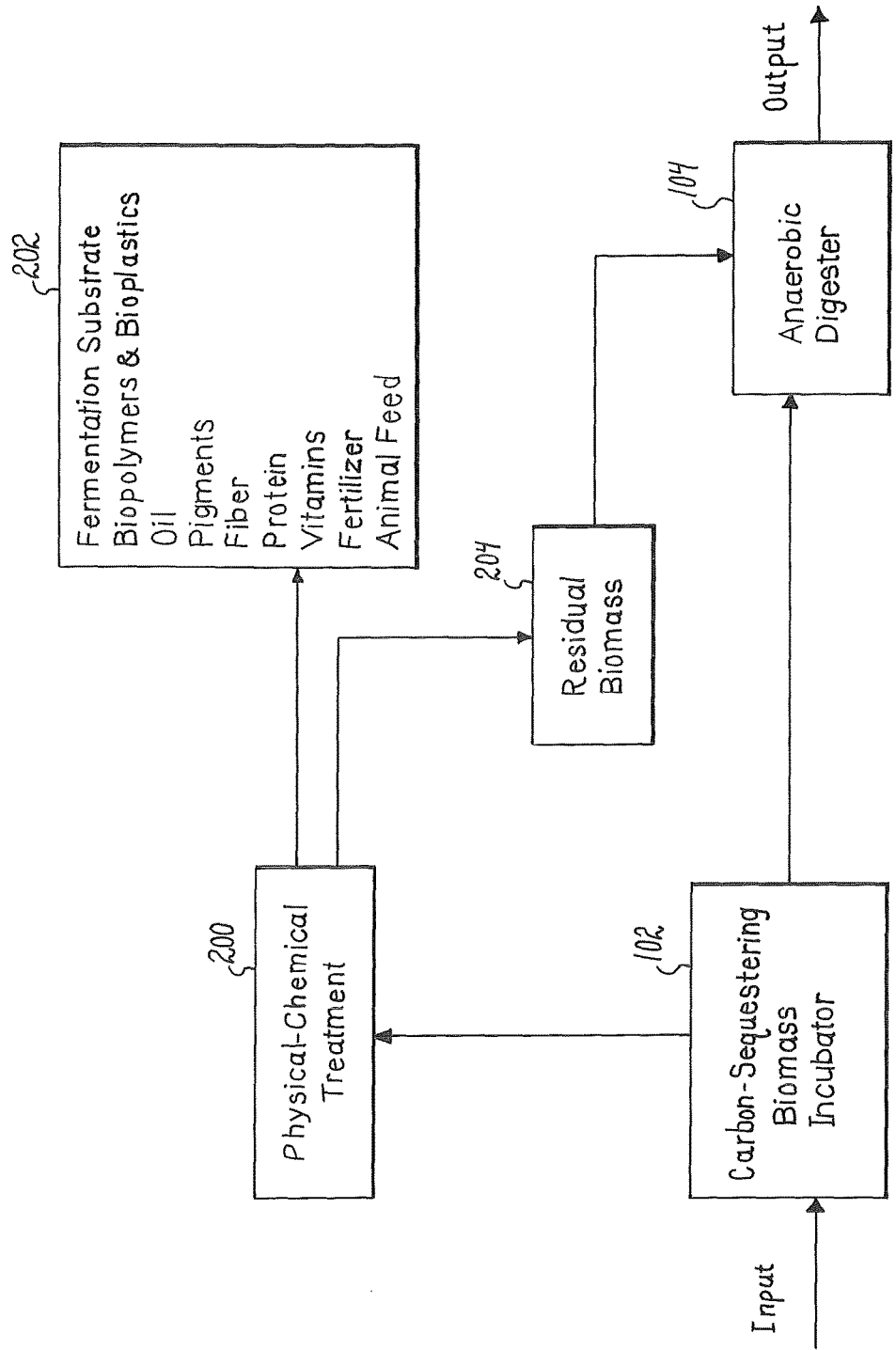
FIG. 4 is a flow diagram of some treatments of a carbon-sequestering biomass.

FIG. 4 illustrates another embodiment of the device 100, wherein at least a portion of the carbon-sequestering biomass produced in the carbon-sequestering biomass incubator 102 can be processed in up to two different processes. Namely, the biomass produced can be directed to physical-chemical treatment 200 and/or to an anaerobic digester 104. In some embodiments, all of the biomass is directed to physical-chemical treatment 200. In some embodiments, a portion of the biomass, such as about 5%, about 10%, about 15%, about 20%, about 25%, about 30%, about 35%, about 40%, about 45%, about 50%, about 60%, about 65%, about 75%, about 80%, about 85%, about 90% or about 95%, is directed to physical-chemical treatment 200 while the remaining biomass is directed to the anaerobic digester 104. In still other embodiments, all of the biomass is directed to the anaerobic digester 104. In a preferred embodiment, the device is configured and arranged such that the amounts of biomass directed to the physical-chemical treatment 200 and/or the anaerobic digester 104 can be modulated or otherwise changed or adjusted, such as depending upon changes in the needs of the manufacturer, the consumer, and the like.

In some embodiments, at least a portion of the carbon-sequestering biomass is removed from the carbon-sequestering biomass incubator 102 for physical-chemical treatment 200. Suitable physical-chemical treatment include but are not limited to heating, acid and/or alkali treatment, maceration, enzymatic degradation, solvent extraction with chemicals or critical $CO_2$, and cell disruption via extreme pressure changes.

A number of products 202 can be produced from the photosynthetic biomass via the physical-chemical treatment 200 described above. Exemplary products include but are not limited to fermentation substrates, biopolymers and bioplastics, oil, pigments, fiber, protein, vitamins, fertilizer and animal feed. Generally, a residual biomass 204 is generated by the physical-chemical treatment 200 of the photosynthetic biomass. The residual biomass 204 is directed to the anaerobic digester 104, where it is digested as described above.

In yet another embodiment, the device 100 is a deep well, stand-along anaerobic bioreactor or digester 104, such as described with regards to FIGS. 1 through 3. For example, with reference to FIGS. 1 and 2, the device 100 lacks the centrally located photosynthetic incubator portion 102. Accordingly, in this embodiment, the device 100 receives a biomass from a separate device, rather than generating the biomass within itself. For example, the biomass may be generated in a separate carbon-capture device. In a further example, a photosynthetic biomass may capture $CO_2$ in an incubator device integrated with a flue gas-handling system. After generation, the biomass is transferred from the incubator and into the anaerobic digester. Subsequently the received biomass is anaerobically digested, such as described above. Methane may be a digestion product, which may be captured and used as a fuel or a raw material, such as is described elsewhere herein. In certain embodiments, the device 100 receives a stream of flue gas, such that the $CO_2$ present in the flue gas is directly converted into methane by the anaerobic process. Suitable microorganisms include, but are not limited to, *Methanobacterium thermoautotrophicum*. It is noted that the pressure is increased within the deep well anaerobic digester 100. Accordingly, the solubility of the $CO_2$ from the flue gas is increased. The increased concentration of the $CO_2$ drives the conversion of the $CO_2$ to methane, such as by the *M. thermoautotrophicum*, towards improved production of the methane from the $CO_2$.

Example 1

An exemplary device 100 has a depth of about 500 ft into the ground and includes an inner reactor, such as the carbon-sequestering biomass incubator 102, with a diameter of about 8 ft surrounded by an outer reactor, such as the anaerobic digester 104, with a diameter of about 15 ft. The inner reactor contains algae with a concentration of about 5,000 mg/dl of incubation liquid or medium. The algae grows at a rate of 2.3 per day. The carbon content of the dry weight is about 50%. The inlet gas, such as into the inner reactor, includes a $CO_2$ content of about 15%. The $CO_2$ transfer efficiency, such as into the liquid, is about 70%. Of the $CO_2$ transferred into the liquid, the biomass takes up about 70% from the liquid. Thus, the $CO_2$ density is about 0.12 $lb/ft^3$.

A number of materials are generated from the biomass in the inner reactor. From an amount of generated biomass, approximately 59% of the fuel and chemicals produced is proteins (dry weight), approximately 19% is fats and oils (dry weight), approximately 13% is carbohydrates (dry weight), and approximately 30% is residual biomass after product recovery (dry weight).

The residual biomass, such as biomass left over after product recovery, is transferred to the outer reactor, such as the anaerobic digester 104, with a loading rate, such as biomass dry weight/reactor volume, of about 0.5 $lb/ft^3$. Approximately 35% of the transferred biomass is destroyed with about 5 $ft^3$ of methane produces per pound of biomass destroyed.

Example 2

An exemplary device 100, similar to that described in Example 1, above, includes a carbon-sequestering biomass incubator 102 with a volume of 63,250 $ft^3$ or 473,110 gal. The incubator 102 supports a biomass inventory of about 19,681 lbs and can produce about 45,267 lb of biomass per day. The produced biomass has a carbon content of about 22,634 lb/day. About 82,990 lb of $CO_2$ is absorbed by the biomass per day. About 118,557 lb of $CO_2$ is transferred into solution per day. The mass of the $CO_2$ in the inlet gas is about 169,367 lb per day, such as 1,411,391 $ft^3$ per day. Accordingly, the inlet gas volume is about 980 scfm.

The biomass generated undergoes physical-chemical treatment 200, such as heating, acid and/or alkali treatment, maceration, enzymatic degradation, solvent extraction with chemicals or critical $CO_2$, and/or cell disruption via extreme pressure changes. Thus, about 26,708 lb (dry weight) of proteins is produced per day. Additionally, about 8,601 lb (dry weight) of fat/oil and about 5,885 lb (dry weight) of carbohydrates is produced per day. The residual biomass after product recover is about 13,580 lb (dry weight) per day.

The residual biomass is transferred to the anaerobic digester 104. The anaerobic digester has a volume of about 25,143 ft$^3$, such as about 188.069 gal. The digester 104 is fed biomass at a rate of about 13,580 lb per day. The biomass fed requires a reactor design volume of about 27,160 ft$^3$. About 4,853 lb of biomass is destroyed per day, to generate about 23,765 ft$^3$ of methane per day. About 8,827 lb of biomass per day is left for ultimate disposal, such as by incineration or in a land fill.

Example 3

An exemplary device 100 for production of methane from carbon dioxide is a deep-well device extending at least 500 feet into the ground. The device 100 includes a $CO^2$-providing apparatus, a photosynthetic bioreactor or incubator 102, for growing a photosynthetic biomass, and an anaerobic digester 104, for digesting at least a portion of the photosynthetic biomass and generating methane as a digestion product. The incubator 102 is located coaxially within the anaerobic digester 104, such that the upper end of the incubator 102 is in fluid flow communication with the upper end of the anaerobic digester 104. The incubator 102 receives $CO_2$ from a $CO_2$ inlet, water and nutrients. A source of light, sufficient for photosynthesis, is located within the incubator 102. The incubator is inoculated with a photosynthetic biomass, which metabolizes at least a portion of the $CO_2$, so as to produce additional photosynthetic biomass. A portion of the photosynthetic biomass overflows into the digester 104. An anaerobic biomass within the digester 104 substantially anaerobically digests the photosynthetic biomass that overflows into the digester 104, and generates methane is a digestion product. The methane is collected by a collecting apparatus associated with the anaerobic digester.

Example 4

An exemplary device 100, similar to that described in Example 1, above, includes a heterotrophic carbon-sequestering biomass incubator 102 with a volume of 63,250 ft$^3$, such as 473,110 gal. The incubator 102 supports a biomass inventory of about 19,681 lbs and can produce about 45,267 lb of biomass per day. The produced biomass has a carbon content of about 22,634 lb/day. About 82,990 lb of chemically derived carbon is absorbed by the biomass per day. About 118,557 lb of carbon is transferred into solution per day. The mass of the carbon in the liquid carbon inlet is about 169,367 lb per day.

The biomass generated undergoes physical-chemical treatment 200, such as heating, acid and/or alkali treatment, maceration, enzymatic degradation, solvent extraction with chemicals or critical $CO_2$, and/or cell disruption via extreme pressure changes. Thus, about 26,708 lb (dry weight) of proteins is produced per day. Additionally, about 8,601 lb (dry weight) of fat/oil and about 5,885 lb (dry weight) of carbohydrates is produced per day. The residual biomass after product recover is about 13,580 lb (dry weight) per day.

The residual biomass is transferred to the anaerobic digester 104. The anaerobic digester has a volume of about 25,143 ft$^3$, such as about 188.069 gal. The digester 104 is fed biomass at a rate of about 13,580 lb per day. The biomass fed requires a reactor design volume of about 27,160 ft$^3$. About 4,853 lb of biomass is destroyed per day, to generate about 23,765 ft$^3$ of methane per day. About 8,827 lb of biomass per day is left for ultimate disposal, such as by incineration or in a land fill.

It is to be understood that while certain forms of the present invention have been illustrated and described herein, it is not to be limited to the specific forms or arrangement of parts described and shown.

What is claimed and desired to be secured by Letters Patent is as follows:

1. A method for sequestering $CO_2$ in a photosynthetic biomass, the method comprising:
   introducing a $CO_2$-laden air stream to a photosynthetic biomass incubator, wherein the photosynthetic biomass incubator contains a photosynthetic biomass;
   allowing the photosynthetic biomass contained within the photosynthetic biomass incubator to metabolize at least some $CO_2$ from the $CO_2$-laden air stream;
   allowing the photosynthetic biomass to expand such that additional photosynthetic biomass is produced;
   exposing the photosynthetic biomass contained within the photosynthetic biomass incubator to a pressure imparted by a vertical column of water in a well extending from ground level to at least at 50 meters below ground level; and
   subjecting at least a portion of the photosynthetic biomass to physical-chemical treatment to recover fat, protein, or carbohydrate.

2. The method of claim 1, further comprising exposing the photosynthetic biomass contained within the photosynthetic biomass incubator to light.

3. The method of claim 2, wherein the light is provided by a light source located within the photosynthetic biomass incubator.

4. The method of claim 3, wherein the light source is a plurality of light emitting diodes.

5. The method of claim 4, wherein the plurality of light emitting diodes are flashed on and off.

6. The method of claim 1, wherein the photosynthetic biomass comprises an organism selected from the group consisting of algae and cyanobacteria.

7. A method for sequestering $CO_2$ in a photosynthetic biomass, the method comprising:
   introducing a $CO_2$-laden air stream to a vertical, cylindrical photosynthetic biomass incubator containing a photosynthetic biomass, wherein the vertical, cylindrical photosynthetic biomass incubator is buried and extends at least 100 meters below ground level;
   allowing the photosynthetic biomass contained within the photosynthetic biomass incubator to metabolize at least some $CO_2$ from the $CO_2$-laden air stream;
   allowing the photosynthetic biomass to expand such that additional photosynthetic biomass is produced;
   exposing the photosynthetic biomass contained within the photosynthetic biomass incubator to a pressure imparted by a vertical column of water in a well extending from ground level to at least at 100 meters below ground level; and
   subjecting at least a portion of the photosynthetic biomass to physical-chemical treatment to recover fat, protein, or carbohydrate.

8. The method of claim 1, wherein the photosynthetic biomass incubator is an above ground pressurized reactor.

9. The method of claim 1, further comprising mixing the photosynthetic biomass contained within the photosynthetic biomass incubator.

10. The method of claim 9, wherein the mixing is provided by a mixing apparatus located within the photosynthetic biomass incubator.

11. The method of claim 10, wherein the mixing apparatus is a circulating pump system, a flow diverter, an incoming fluid sparger, a jet nozzle, an eductor, a pulse air mixer, a paddle, or a combination thereof.

12. The method of claim 1, further comprising delivering a fluid outflow from the photosynthetic biomass incubator to a digester containing a plurality of methanogenic microorganisms.

13. The method of claim 12, wherein the digester is operable to at least partially convert the portion of the photosynthetic biomass within the fluid outflow to methane.

14. The method of claim 12, wherein the plurality of methanogenic microorganisms are exposed to a pressure greater than atmospheric pressure.

15. The method of claim 1, further comprising subjecting at least a portion of the biomass to physical-chemical treatment to produce a product selected from the group consisting of a fermentation substrate, a biopolymer, a bioplastic, an oil, a pigment, a fiber, a protein, a vitamin, a fertilizer and an animal feed.

16. The method of claim 1, further comprising modulating the pressure in the photosynthetic biomass incubator.

17. The method of claim 1, further comprising releasing the pressure in the photosynthetic biomass incubator.

18. The method of claim 17, wherein the pressure is released by withdrawing liquid from the photosynthetic biomass incubator.

19. The method of claim 1, further comprising increasing the pressure in the photosynthetic biomass incubator.

20. A method for sequestering carbon in a biomass, the method comprising:
   introducing a carbon source to a biomass incubator, wherein the biomass incubator contains a biomass;
   allowing the biomass contained within the biomass incubator to metabolize at least some carbon from the carbon source;
   allowing the biomass to expand such that additional biomass is produced;
   exposing the biomass contained within the biomass incubator to a pressure imparted by a vertical column of water in a well extending from ground level to at least at 50 meters below ground level; and
   subjecting at least a portion of the biomass to physical-chemical treatment to recover fat, protein, or carbohydrate.

21. The method of claim 20, wherein the biomass is a heterotrophic biomass comprising an organism selected from the group consisting of micro-algae, yeast and bacteria.

22. The method of claim 20, further comprising removing a metal or other contaminant by absorption of the metal or other contaminant onto the biomass.

23. The method of claim 20, further comprising exposing the biomass to a nutrient.

24. The method of claim 7, further comprising exposing the photosynthetic biomass contained within the vertical, cylindrical photosynthetic biomass incubator to light from a light source located within the vertical, cylindrical photosynthetic biomass incubator.

* * * * *